United States Patent [19]

Li et al.

[11] Patent Number: 5,053,504

[45] Date of Patent: Oct. 1, 1991

[54] PROCESS FOR BENZAZEPINE INTERMEDIATES

[75] Inventors: Wen-Sen Li, Bensalem, Pa.; John K. Thottathil, Robbinsville, N.J.; Michael Murphy, Warwick, N.Y.

[73] Assignee: E. R. Squibb & Sons, Inc., Princeton, N.J.

[21] Appl. No.: 442,822

[22] Filed: Nov. 29, 1989

[51] Int. Cl.$^5$ ............... C07D 267/10; C07D 295/12; C07D 413/12; C07D 413/14; C07D 413/10; C07D 213/46; C07D 207/333; C07D 233/60; C07D 307/28; C07D 333/16; C07D 277/24

[52] U.S. Cl. .................... 540/488; 544/130; 544/131; 544/133; 544/139; 544/141; 544/146; 544/152; 544/158; 544/159; 544/160; 544/161; 544/163; 544/165; 544/167; 544/168; 544/169; 544/171; 546/189; 546/194; 546/208; 546/209; 546/210; 546/213; 546/214; 546/226; 546/230; 546/234; 546/235; 546/237; 546/239; 546/255; 546/278; 546/280; 546/281; 546/283; 546/284; 546/304; 546/306; 546/309; 546/312; 546/316; 546/323; 546/328; 546/330; 546/335; 546/337; 548/196; 548/200; 548/336; 548/337; 548/341; 548/343; 548/517; 548/518; 548/524; 548/527; 548/531; 548/537; 548/538; 548/557; 548/558; 549/59; 549/60; 549/69; 549/72; 549/473; 549/480; 549/487; 560/21

[58] Field of Search ............... 540/488; 544/130, 131, 544/133, 139, 141, 146, 152, 158, 159, 160, 161, 163, 165, 167, 168, 169, 171; 546/245, 189, 194, 208, 209, 210, 213, 214, 226, 230, 234, 235, 237, 239, 255, 278, 280, 281, 283, 284, 304, 306, 309, 312, 316, 323, 328, 330, 335, 337; 548/531, 196, 200, 336, 337, 341, 343, 517, 518, 524, 527, 531, 537, 538, 557, 558; 560/21, 22; 549/59, 60, 69, 72, 47, 3, 480, 487

[56] References Cited

U.S. PATENT DOCUMENTS 4,748,329  5/1988  Floyd et al. .................. 540/523

OTHER PUBLICATIONS

L. A. Carpino et al., "Convenient Source of 'Naked' Fluoride: Tetra-n-Butylammonium Chloride and Potassium Fluoride Dihydrate", *J.C.S. Chem. Comm*, 1979, pp. 514–515.

S. Colonna et al., "Asymmetric Induction in the Base-Catalysed Michael Addition of Nitromethane to Chalcone", *J.S.C. Chem. Comm.*, 1978, pp. 238–239.

J. H. Cark, "Fluroide Ion as a Base in Organic Synthesis", *Chem. Rev.*, 1980, 80, pp. 429–452.

Bartoli et al., *J. Org. Chem.*, 1987, 52, 4381–4384.

*Primary Examiner*—Mary C. Lee
*Assistant Examiner*—Patricia L. Morris
*Attorney, Agent, or Firm*—Theodore R. Furman, Jr.

[57] ABSTRACT

A process is disclosed for providing benzazepine intermediates of the formulae

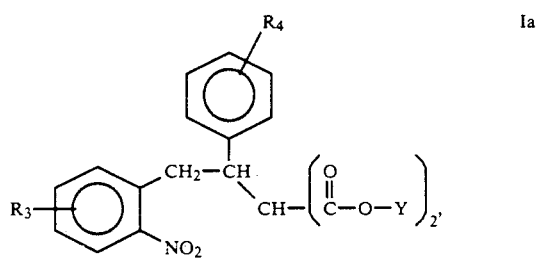

and

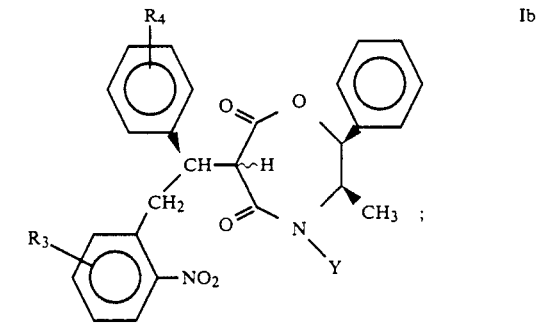

wherein $R_3$, $R_4$ and Y are as defined herein, which intermediates are useful in a process for the preparation of pharmaceutically useful benzazepine derivatives.

2 Claims, No Drawings

PROCESS FOR BENZAZEPINE INTERMEDIATES

BRIEF DESCRIPTION OF THE INVENTION

A novel process is disclosed for preparing compounds of the formula

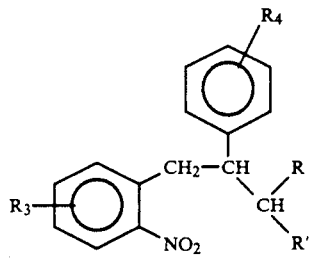   I wherein R and R' are each

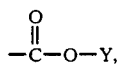

that is

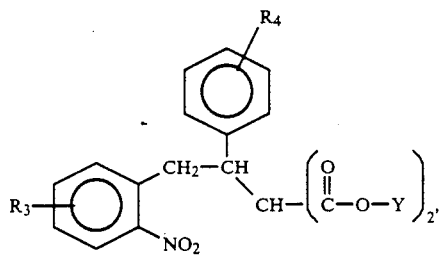   Ia or wherein R and R' together with the methylene group to which they are attached form the ring system

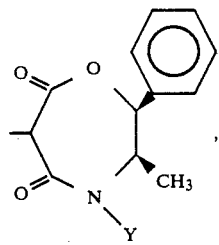

that is

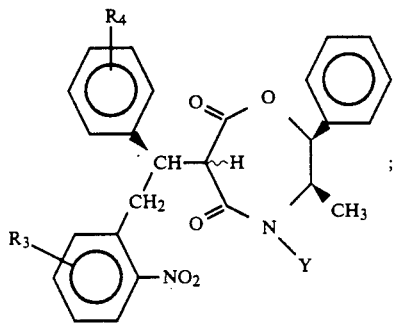   Ib wherein Y is alkyl; $R_3$ is hydrogen, halogen, alkoxy, cyano,

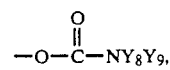

fluoro substituted alkoxy, fluoro substituted alkyl, $-NO_2$, $-NY_{10}Y_{11}$, $-S(O)_m$alkyl, $-S(O)_m$aryl,

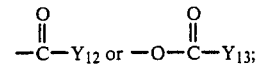

$R_4$ is hydrogen, halogen, alkyl, alkoxy, aryloxy, arylalkoxy, arylalkyl, cyano, hydroxy, alkanoyloxy,

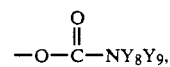

fluorosubstituted alkoxy, fluorosubstituted alkyl, (cycloalkyl)alkoxy, $-NO_2$, $-NY_{10}Y_{11}$, $-S(O)_m$alkyl, $-S(O)_m$aryl,

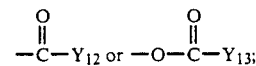

m is zero, one or two; $Y_8$ and $Y_9$ are each independently hydrogen, aryl, alkyl or heteroaryl or $Y_8$ and $Y_9$ taken together with the nitrogen atom to which they are attached are pyrrolidinyl, piperidinyl or morpholinyl; $Y_{10}$ and $Y_{11}$ are each independently hydrogen, alkyl, alkanoyl, arylcarbonyl, heteroarylcarbonyl or

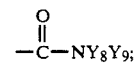

$Y_{12}$ is hydroxy, alkoxy, aryloxy, amino, alkylamino or dialkylamino; and $Y_{13}$ is alkyl, alkoxy or aryloxy.

Further in accordance with the present invention, novel processes are disclosed for preparing the racemic benzazepine derivatives

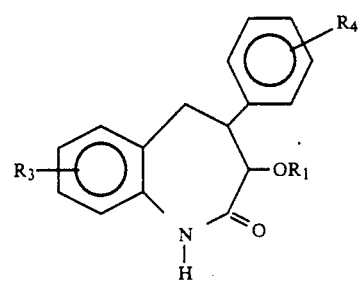   II using compounds of formula Ia, or the optically active benzazepine derivatives

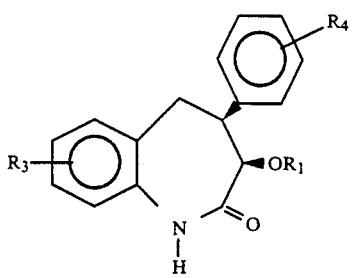

II' using compounds of formula Ib which derivatives are useful, for example, as intermediates in the preparation of many pharmaceutically useful benzazepine compounds.

Compounds of formula Ia are prepared by coupling a compound of the formula

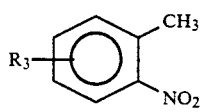

III with a compound of the formula

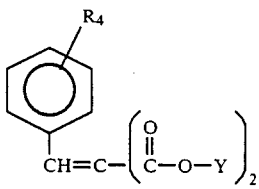

IV in the presence of a source of fluoride ion.

Compounds of formula Ib are prepared by coupling a compound of formula III to a compound of the formula

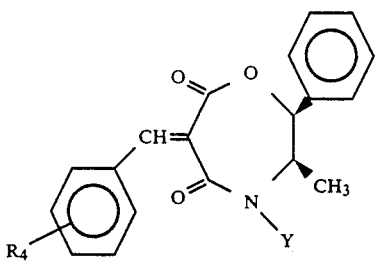

V in the presence of a source of fluoride ion.

DETAILED DESCRIPTION OF THE INVENTION

U.S. Pat. No. 4,748,239, describes the preparation of compounds of formula Ia by reaction of compounds of formula III with compounds of formula IV using a strong base, such as sodium hydride. The use of sodium hydride, or any strong base, provides that greater care must be exercised when employing such a process. The prior art teaches, however, that a strong base should be utilized for the best yields. Unexpectedly, it has been found that a source of fluoride ion used in place of the strong base provides a good yield of compounds of formula Ia. Any source of fluoride ion could be employed and suitable sources include the fluoride ion in the form of neutral compounds, such as tetra-n-butyl- ammonium fluoride (TBAF), potassium fluoride, cesium fluoride and benzyltrimethyl ammonium fluoride or similar fluoride salts. Preferably, an anhydrous form of the fluoride ion is provided to better facilitate the present process. This can be accomplished by using the above sources of fluoride ion in their anhydrous form or by using hydrated forms of the fluoride ion source in conjunction with, for example, molecular sieves and/or potassium carbonate to remove water. The reaction of compound III with compound IV in the presence of a source of fluoride ion can also employ one or more solvents, e.g., tetrahydrofuran, dioxane, ether, dimethylformamide or similar solvents.

The present process also offers a distinct advantage over the prior art in that high yields of the intermediates of formula Ib with high optical purity are provided. The ability to produce optically pure compounds of formula Ib facilitates a more efficient and more economical production of optically active intermediates of formula II' and of pharmaceutically important cis benzazepine derivatives which can be represented by the general formula

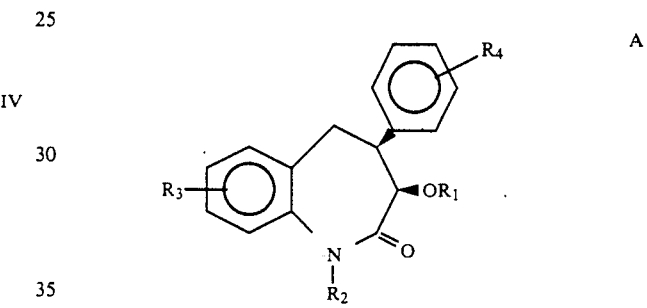

A

As discussed previously, the first step of the present process to prepare compounds of formula Ib involves coupling a compound of formula III with a compound of formula V in the presence of a source of fluoride ion. (The preparation of compounds of formula V have been described in T. Mukaiyama, T. Takeda and K. Fujimoto; *Bull. Chem. Soc. Jpn.*, 51, 3368 (1978).) This is conveniently carried out in an organic solvent, such as tetrahydrofuran, ether or dimethylformamide. Any source of fluoride ion could be employed and suitable sources include tetra-n-butylammonium fluoride (TBAF), potassium fluoride, cesium fluoride and benzyltrimethyl ammonium fluoride or similar fluoride salts. Preferably, an anhydrous form of the fluoride ion is provided to better facilitate the present process. This can be accomplished by using the above sources of fluoride ion in their anhydrous form or by using hydrated forms of the fluoride ion source in conjunction with, for example, molecular sieves and potassium carbonate to remove water.

Reaction of compounds of formula Ib, wherein Y is methyl, with an alcohol of the formula Y—OH, wherein Y is alkyl, preferably methyl, conveniently carried out in alcohol as solvent and in the presence of a base, e.g., potassium carbonate, followed by reduction accomplished by art-recognized techniques such as catalytic hydrogenation, for example, in the presence of palladium on carbon catalyst, or by using a chemical reducing agent (e.g., ferrous sulfate or stannous chloride), provides a novel intermediate of the formula

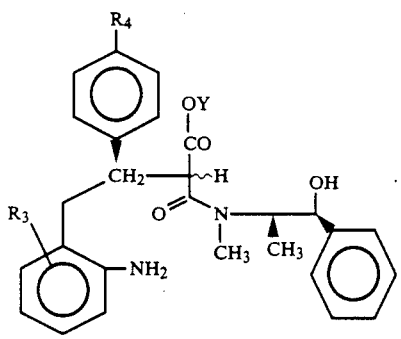

VI

Treating the compound of formula VI with a chlorinating agent, e.g., thionyl chloride, provides the optically active trans compounds of the formula

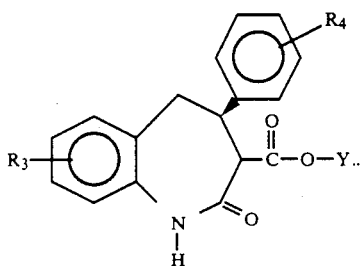

VII

Compound VII can thereafter be reacted, as described in U.S. Pat. No. 4,748,239, with a strong base (e.g., lithium diisopropylamide, potassium hexamethyldisilazide or potassium t-amylate) in an ethereal solvent (e.g., tetrahydrofuran) or a polar solvent (e.g., dimethylformamide) at low temperatures in the presence of anhydrous oxygen gas and a reducing agent (e.g., a trialkylphosphite, such as triethylphosphite) to provide

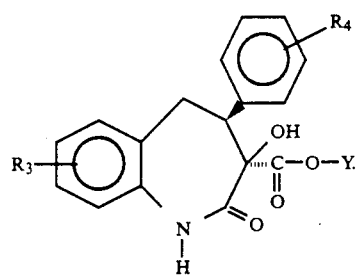

VIII

Decarboxylation of compound VIII, for example by treatment with excess lithium iodide in hot pyridine, or hot dimethylformamide, provides optically active cis isomer of the formula

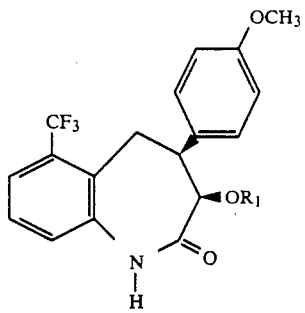

II' wherein $R_1$ is hydrogen. The present process provides yields of about 65% or greater with optical purities exceeding 95%.

To prepare racemic compounds of formula II, compounds of formula Ia can be reduced, as described in U.S. Pat. No. 4,748,239 to provide compounds of the formula

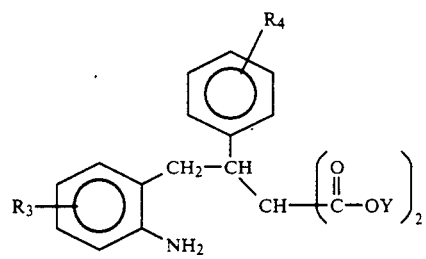

IX which can be accomplished by known techniques such as by catalytic hydrogenation, for example, by using palladium on charcoal as a catalyst or by using a chemical reducing agent such as ferrous sulfate or stannous chloride.

Treatment of compounds of formula IX with an alkali metal alkoxide (e.g., sodium methoxide) and an alcohol (e.g., methanol) provides compounds of the formula

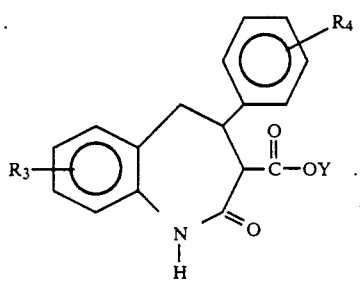

X

Treatment of compound X as compound VII, above, provides a racemic compound of the formula

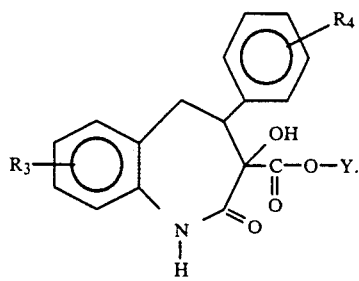

XI

Correspondingly, treatment of compound XI as compound VIII, above, provides a racemic compound

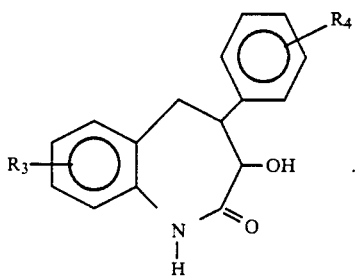

XII

Compound XII can either be resolved or can be used as the racemic alcohol in subsequent methodology.

Preparation of the compounds of formula Ia, Ib, II and II' are particularly useful as part of a larger process for preparing benzazepine derivatives, such as those in U.S. Pat. Nos. 4,748,239, 4,771,047, 4,767,756 and copending application Ser. No. 353,806, filed May 22, 1989 now U.S. Pat. No. 4,902,684 entitled "BENZAZEPINE AND BENZOTHIAZEPINE DERIVATIVES" having the general formula

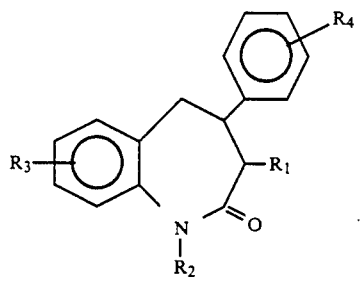

A as illustrated above.

For example, Ser. No. 353,806 covers compounds of formula A wherein $R_1$ is

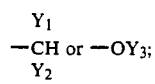

$R_2$ is

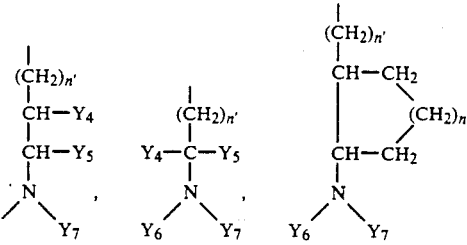

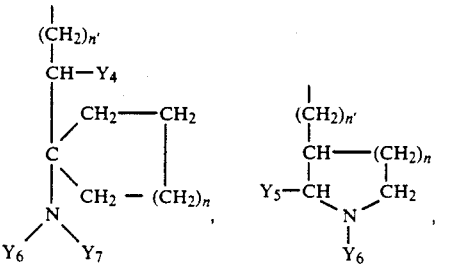

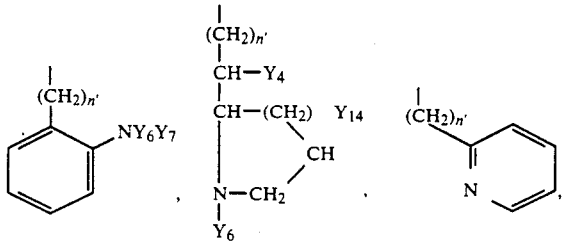

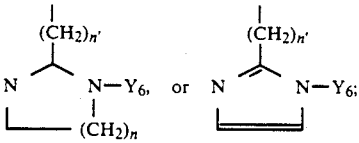

$R_3$ is hydrogen, halogen, alkoxy, cyano,

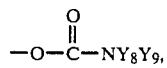

fluoro substituted alkoxy, fluoro substituted alkyl, $-NO_2$, $-NY_{10}Y_{11}$, $-S(O)_m$alkyl, $-S(O)_m$aryl,

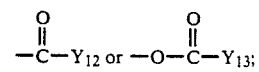

$R_4$ is hydrogen, halogen, alkoxy, aryloxy, cyano,

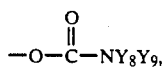

fluoro substituted alkoxy, fluoro substituted alkyl, $-NO_2$, $-NY_{10}Y_{11}$, $-S(O)_m$alkyl, $-S(O)_m$aryl,

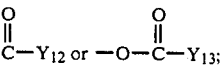

n or n' are independently 0, 1, 2 or 3;
m is 0, 1 or 2;

$Y_1$ and $Y_2$ are independently hydrogen or alkyl, $Y_1$ is hydrogen and $Y_2$ is alkenyl, alkynyl, aryl, heteroaryl, or cycloalkyl, or $Y_1$ and $Y_2$ together with the carbon atom to which they are attached are cycloalkyl;

$Y_3$ is hydrogen, alkyl, alkanoyl, alkenyl, arylcarbonyl, heteroarylcarbonyl, or

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ and $Y_7$ are each independently hydrogen, alkyl, cycloalkyl or arylalkyl or $Y_6$ and $Y_7$ together with the nitrogen atom to which they are attached are azetidinyl, pyrrolidinyl, piperidinyl, or morpholinyl;

$Y_8$ and $Y_9$ are each independently hydrogen, alkyl, aryl or heteroaryl, or $Y_8$ and $Y_9$ together with the nitrogen atom to which they are attached are pyrrolidinyl, piperidinyl or morpholinyl;

$Y_{10}$ and $Y_{11}$ are each independently hydrogen, alkyl, alkanoyl, arylcarbonyl, heteroarylcarbonyl, or

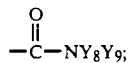

$Y_{12}$ is hydroxy, alkoxy, aryloxy, amino, alkylamino or dialkylamino;

$Y_{13}$ is alkyl, alkoxy or aryloxy; and, $Y_{14}$ is hydrogen, hydroxy, alkoxy, aryloxy or arylalkoxy.

This cis form is preferred due to greater activity.

Most preferred are compounds of the formula

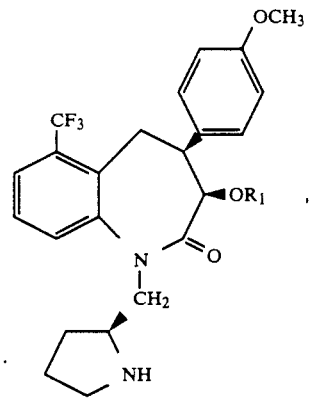

wherein $R_1$ is hydrogen or acetyl, which are useful as cardiovascular agents.

In providing the products of formula A' using the intermediates of formula Ia, the corresponding intermediates of racemic XII, i.e.

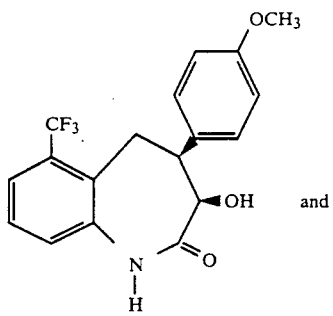

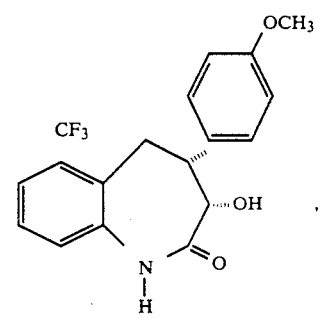

can be separated using known techniques to obtain the desired optically active cis isomer XIIa', or can be used as a racemic mixture.

Compound XIIa', or the racemic mixture, can be coupled with a compound of the formula

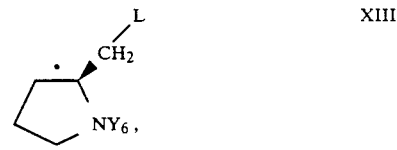

(wherein L is a leaving group, such as halogen or tosyloxy, preferably tosyloxy and wherein $Y_6$ is other than hydrogen and serves as a protecting group) to provide compounds of formula A' where $R_1$ is hydrogen following standard deprotection to obtain the compounds where $Y_6$ is hydrogen.

Convention acylation techniques can be employed to provide compounds of formula A' wherein $R_1$ is acetyl.

If compounds of formula A' have been obtained as a racemic mixture, the isomers can be separated by known techniques to provide the desired cis isomer.

Alternatively, compounds of formula A' can be provided via the process utilizing novel intermediate Ib to arrive at intermediate optically active II' as described above. The cis benzazepine II' compound can be coupled with compound XIII as described above.

EXAMPLE 1

(3S-trans)-2,3,4,5-Tetrahydro-4-(4-methoxyphenyl)-2-oxo-6-(trifluoromethyl)-1H-1-benzazepine-3-carboxylic acid, methyl ester

A.

[2S-[2α,3α,6(S*)]]-3,4-Dihydro-6-[1-(4-methoxyphenyl)-2-[2-nitro-6-(trifluoromethyl)phenyl]ethyl]-3,4-dimethyl-2-phenyl-1,4-oxazepine-5,7(2H,6H)-dione To a vigorously stirring mixture of molecular sieves (34.2 g), potassium carbonate (11.4 g), and tetra-n-butylammonium fluoride (5.75 g, 18.24 mmol) was added dropwise trifluoromethyl nitrotoluene (2.77 ml, 18.24 mmol) at 0° C. Then a tetrahydrofuran (10 ml) solution of (2S-cis)-3,4-Dihydro-6-[(4-methoxyphenyl)-methylene]-3,4-dimethyl-2-phenyl-1,4-oxazepine-5,7(2H,6H)-dione (3.98 g, 11.4 mmol) was added dropwise to this mixture at the same temperature. After complete addition, the reaction mixture was stirred at ~4° C. for 16 hours and then quenched with 100 ml 30% aqueous acetic acid. The solid was filtered and washed thoroughly by ethyl acetate. The combined organic layer was washed with sodium hydrogen carbonate, brine and dried over magnesium sulfate. Column chromatography (50% ethyl ether/hexane) gave 5.09 g of the title A compound and 380 mg of the trans isomer.

$^1$H NMR: δ 7.80 (d, 1H), 7.69 (d, 1H), 7.30 (M, 6H), 6.85 (d, 2H), 6.60 (d, 2H), 5.48 (S, 1H), 4.23 (d, 1H), 4.01 (d, 1H), 3.73 (M, 1H), 3.63 (S, 3H), 3.54 (dd, 1H) 3.09 (S, 3H), 1.13 (d, 3H) ppm.

$^{13}$C NMR: δ 167, 165, 159, 152, 136, 133, 130 (M), 129, 128, 127.6 (M), 125, 114, 78, 64, 63, 55, 48, 37, 32, 12 ppm. M.S. (m/e): (M+H), 557 (100), 537 (10), 398 (10), 234 (20).

B.

(βR)-α-[[(2-Hydroxy-1-methyl-2-phenylethyl)methylamino]carbonyl]-β-(4-methoxyphenyl)-2-nitro-6-(trifluoromethyl)benzenebutanoic acid, methyl ester 24 mg Anhydrous potassium carbonate was added to a methanol (9 ml) solution of the title A compound (1.9 g, 3.42 mmol) until the potassium carbonate was totally dissolved. The reaction solution was stirred for an additional 15 minutes. The reaction was diluted with excess ether. The resulting precipitate was filtered and the filtrate was washed with brine, dried over magnesium sulfate. Concentration provided a quantitative yield of the title B compound.

C.

(βR)-2-Amino-β-[[(2-hydroxy-1-methyl-2-phenylethyl)methylamino]carbonyl]-β-(4-methoxyphenyl)-6-(trifluoromethyl)benzenebutanoic acid, methyl ester The title B compound (300 mg, 0.51 mmol) without purification was subjected to 10% palladium on carbon catalyst (30 mg) in methanol (6 ml). This solution was degassed by evacuation of air and by refilling with argon 3 times, then argon was replaced with hydrogen via a balloon. It was stirred for 4 hours. The reaction was filtered through a pad of Celite and concentration gave 300 mg of the title C compound.

D.

(3S-trans)-2,3,4,5-Tetrahydro-4-(4-methoxyphenyl)-2-oxo-6-(trifluoromethyl)-1H-1-benzazepine-3-carboxylic acid, methyl ester To a stirred methylene chloride (0.6 ml) solution of the title C compound (160 mg, 0.251 mmol) was added dropwise thionyl chloride (23 μl, 0.314 mmol). The reaction mixture was stirred for 72 hours and then diluted with ether and washed with water, brine, dried over magnesium sulfate. Concentration gave 74 mg of the title compound (75%). [α]$_D$= +10.5 (c 1, MeOH), optical purity greater than 95%.

$^1$H NMR: δ 8.11(s, 1H), 7.53 (d, 1H), 7.35 (t, 1H), 7.22 (m, 3H), 6.86 (d, 1H), 4.29 (m, 1H), 3.80 (s, 3H), 3.73 (d, 1H), 3.42 (s, 3H), 3.30 (dd, 1H), 3.10 (dd, 1H) ppm.

EXAMPLE 2

[1-(4-Methoxyphenyl)-2-[2-nitro-6-(trifluoromethyl)-phenyl]ethyl]propanedioic acid, dimethyl ester To a vigorously stirring mixture of molecular sieves (5.25 g) and tetra-n-butylammonium fluoride (0.882 g) was added dry tetrahydrofuran (10 ml) at 0° C. 2-Methyl-1-nitro-3-(trifluoromethyl)benzene (0.425 ml; 2.8 mmol) was added to the suspension followed by the addition of a solution of 2-[(4-methoxyphenyl)methylene]propanedioic acid, dimethyl ester (0.44 g; 1.75 mmol) in 5 ml of tetrahydrofuran. After 30 minutes of 0° C. the reaction was brought to room temperature and stirred for another 20 minutes. The reaction was quenched with 30% acetic acid until a light yellow color was observed and thereafter was diluted with 45 ml of ethyl ether, filtered and washed twice with 30 ml of ethyl ether. The combined organic solution was washed with sodium hydrogen carbonate and dried over magnesium sulfate. Concentration and chromatography provided 0.72 g of the title compound as a foam.

$^1$H NMR: δ 7.82 (d, 1H), 7.73 (d, 1H), 7.39 (t, 1H), 6.83 (d, 1H), 6.67 (d, 1H), 3.86 (m, 1H), 3.77 (s x2, 6H), 3.58 (m, 3H), 3.42 (s, 3H) ppm. $^{13}$C NMR: δ 168, 167, 159, 152, 133, 132, 130(m), 129, 128, 127, 114, 58, 55, 53, 52, 45, 32 ppm. IR (CHCl$_3$), ν(max): 3040, 3000, 2955, 2846, 1738(s), 1611, 1536(s), 1306(s), 1256(s), 1159(s), 1140(s), 830, 690.

MS, (m/e): (M+H), 456, 426, 406, 324(100), 294, 251.

We claim:

1. A process for preparing a compound of the formula

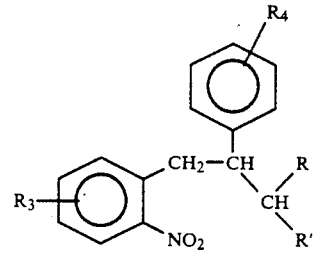

wherein R and R' are each

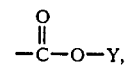

that is

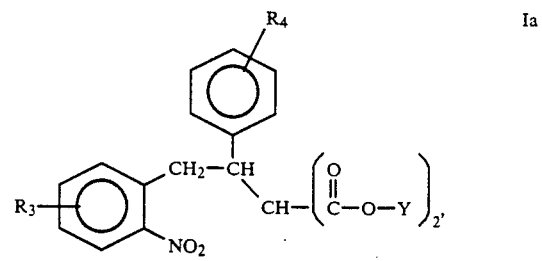

or wherein R and R' together with the methylene group to which they are attached form the ring system

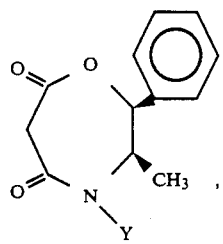

that is

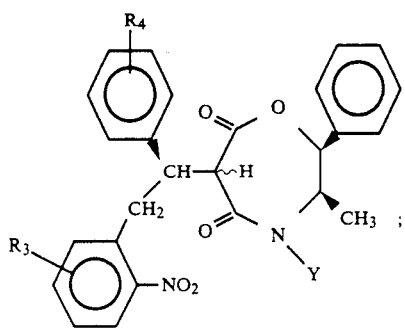

wherein Y is alkyl; $R_3$ is hydrogen, halogen, alkoxy, cyano,

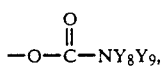

fluoro substituted alkoxy, fluoro substituted alkyl, $-NO_2$, $-NY_{10}Y_{11}$, $-S(O)_m$alkyl, $-S(O)_m$aryl,

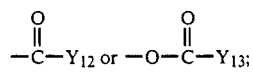

$R_4$ is hydrogen, halogen, alkyl, alkoxy, aryloxy, arylalkoxy, arylalkyl, cyano, hydroxy, alkanoyloxy,

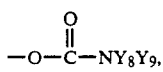

fluorosubstituted alkoxy, fluorosubstituted alkyl, (cycloalkyl)alkoxy, $-NO_2$, $-NY_{10}Y_{11}$, $-S(O)_m$alkyl, $-S(O)_m$aryl,

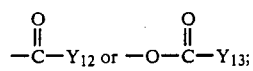

m is zero, one or two; $Y_8$ and $Y_9$ are each independently hydrogen, aryl, alkyl or heteroaryl or $Y_8$ and $Y_9$ taken together with the nitrogen atom to which they are attached are pyrrolidinyl, piperidinyl or morpholinyl; $Y_{10}$ and $Y_{11}$ are each independently hydrogen, alkyl, alkanoyl, arylcarbonyl, heteroarylcarbonyl or

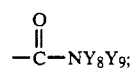

$Y_{12}$ is hydroxy, alkoxy, aryloxy, amino, alkylamino or dialkylamino; and $Y_{13}$ is alkyl, alkoxy or aryloxy; comprising coupling a compound of the formula

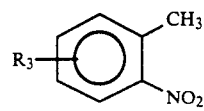

with a compound of the formula

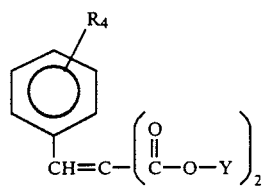

in the presence of a source of fluoride ion; or, coupling a compound of the formula

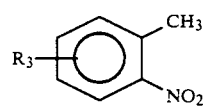

to a compound of the formula

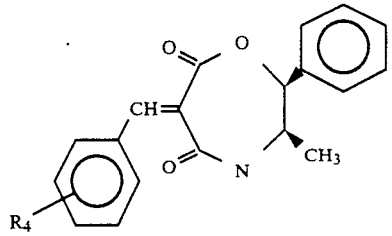

in the presence of a fluoride ion; wherein
the term "heteroaryl" refers to an aromatic heterocycle selected from the group consisting of pyridinyl, pyrrolyl, imidazolyl, furyl, thienyl and thaizolyl; and,
the term "aryl" refers to phenyl and phenyl substituted with 1, 2 or 3 substituents wherein the substituents are independently selected from the group consisting of amino, alkylamino, dialkylamino, nitro, halo, hydroxy, trifluoromethyl, $C_{1-4}$alkyl, $C_{1-4}$alkoxy, alkanoyloxy, carbamoyl and carboxy.

2. The process of claim 1 wherein said source of fluoride ion is selected from tetra-n-butylammonium fluoride, potassium fluoride, cesium fluoride and benzyltrimethylammonium fluoride.

* * * * *